(12) United States Patent
Rapoport et al.

(10) Patent No.: US 9,770,188 B2
(45) Date of Patent: *Sep. 26, 2017

(54) MRI WITH MAGNET ASSEMBLY ADAPTED FOR CONVENIENT SCANNING OF LABORATORY ANIMALS

(71) Applicant: Aspect Imaging Ltd., Shoham (IL)

(72) Inventors: Uri Rapoport, Moshav Ben Shemen (IL); Itzhak Rabinovitz, Ness Tsiyona (IL)

(73) Assignee: ASPECT IMAGING LTD., Shoham (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/375,088

(22) Filed: Dec. 11, 2016

(65) Prior Publication Data
US 2017/0086706 A1    Mar. 30, 2017

Related U.S. Application Data

(63) Continuation of application No. 14/581,266, filed on Dec. 23, 2014, now Pat. No. 9,655,542, which is a
(Continued)

(51) Int. Cl.
*A61B 5/05*    (2006.01)
*A61B 5/055*    (2006.01)
(Continued)

(52) U.S. Cl.
CPC ............. *A61B 5/0555* (2013.01); *A01K 1/03* (2013.01); *A01K 1/0613* (2013.01); *A61D 3/00* (2013.01);
(Continued)

(58) Field of Classification Search
CPC .. A61B 5/0555; G01R 33/3628; G01R 35/00; G01R 33/30; G01R 33/341; G01R 33/383; A01K 1/0613; A01K 1/03
See application file for complete search history.

(56) References Cited

U.S. PATENT DOCUMENTS 3,367,632 A    2/1968    Vail
3,986,480 A    10/1976    Vail
(Continued)

OTHER PUBLICATIONS

"MR-Technology Information Portal"; Retrieved at <<http://www.mr-tip.com>>, Sep. 23, 2011.
(Continued)

*Primary Examiner* — Bo J Peng
(74) *Attorney, Agent, or Firm* — Pearl Cohen Zedek Latzer Baratz LLP

(57) ABSTRACT

An animal handling system (AMS), for positioning an immobilized animal in a predefined configuration therein, comprising an automated tuning unit, including: a proximal portion, held outside a medical device including: at least one inner shaft and at least one outer shaft, the at least one inner is telescopically maneuverable within the at least one outer shaft providing a variable telescopic mechanism; and a distal portion including: a configurable encapsuable life support system (ELSS), the ELSS is rotatable about a longitudinal axis of the at least outer shaft and the at least inner shaft and translationally moveable parallel to the longitudinal axis by means of the maneuverable telescopic mechanism.

6 Claims, 6 Drawing Sheets

Related U.S. Application Data continuation-in-part of application No. 13/241,378, filed on Sep. 23, 2011, now Pat. No. 8,950,363.

(60) Provisional application No. 61/387,538, filed on Sep. 29, 2010.

(51) Int. Cl.
| | | |
|---|---|---|
| *A61D 3/00* | (2006.01) | |
| *G01R 33/30* | (2006.01) | |
| *G01R 33/36* | (2006.01) | |
| *G01R 33/58* | (2006.01) | |
| *A01K 1/06* | (2006.01) | |
| *A01K 1/03* | (2006.01) | |

(52) U.S. Cl.
CPC ......... *G01R 33/30* (2013.01); *G01R 33/3628* (2013.01); *G01R 33/583* (2013.01); *A61B 2503/40* (2013.01); *A61B 2503/42* (2013.01)

(56) References Cited

U.S. PATENT DOCUMENTS

| | | |
|---|---|---|
| 4,084,814 A | 4/1978 | Boggild |
| 4,332,244 A | 6/1982 | Levy et al. |
| 4,771,785 A | 9/1988 | Duer |
| 4,875,485 A | 10/1989 | Matsutani |
| 5,085,219 A | 2/1992 | Ortendahl et al. |
| 5,167,160 A | 12/1992 | Hall, II |
| 6,137,291 A | 10/2000 | Szumowski et al. |
| 6,609,325 B2 | 8/2003 | Harris |
| 7,121,229 B2 | 10/2006 | Hong |
| 7,345,483 B2 | 3/2008 | Vaughan |
| 8,342,136 B2 | 1/2013 | Hadjioannou et al. |
| 8,807,084 B2 | 8/2014 | Rapoport et al. |
| 8,851,018 B2 | 10/2014 | Rapoport et al. |
| 8,896,310 B2 | 11/2014 | Rapoport |
| 2010/0198047 A1 | 8/2010 | Zagorchev et al. |
| 2011/0162652 A1 | 7/2011 | Rapoport |
| 2011/0186049 A1 | 8/2011 | Rapoport |
| 2011/0234347 A1 | 9/2011 | Rapoport |
| 2011/0304333 A1 | 12/2011 | Rapoport |
| 2012/0071745 A1 | 3/2012 | Rapoport |
| 2012/0073509 A1 | 3/2012 | Rapoport et al. |
| 2012/0073511 A1 | 3/2012 | Rapoport et al. |
| 2012/0077707 A1 | 3/2012 | Rapoport |
| 2012/0119742 A1 | 5/2012 | Rapoport |
| 2012/0278990 A1 | 11/2012 | Lanz et al. |
| 2012/0330130 A1 | 12/2012 | Lanz et al. |
| 2013/0079624 A1 | 3/2013 | Rapoport |
| 2013/0109956 A1 | 5/2013 | Rapoport |
| 2013/0237803 A1 | 9/2013 | Rapoport |
| 2013/0328559 A1 | 12/2013 | Rapoport |
| 2013/0328560 A1 | 12/2013 | Rapoport |
| 2013/0328563 A1 | 12/2013 | Rapoport |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051976 A1 | 2/2014 | Rapoport et al. |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0142914 A1 | 5/2014 | Rapoport |
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0230850 A1 | 8/2014 | Rapoport |
| 2014/0257081 A1 | 9/2014 | Rapoport |
| 2014/0266203 A1 | 9/2014 | Rapoport |
| 2014/0300358 A1 | 10/2014 | Rapoport |
| 2014/0378821 A1 | 12/2014 | Rapoport et al. |
| 2014/0378825 A1 | 12/2014 | Rapoport et al. |
| 2015/0059655 A1 | 3/2015 | Rapoport |
| 2015/0065788 A1 | 3/2015 | Rapoport |
| 2015/0077105 A1 | 3/2015 | Rapoport et al. |

OTHER PUBLICATIONS

Final office action of U.S. Appl. No. 13/241,378, dated Feb. 24, 2014.
Non-final office action of U.S. Appl. No. 13/241,378, dated Sep. 26, 2011.
Aspect Imaging Ltd., "Shutting Assembly for Closing an Entrance of an MRI Device", co-pending U.S. Appl. No. 14/540,163, filed Nov. 13, 2014.
Aspect Imaging Ltd., "MRI-Incubator's Closure Assembly", co-pending U.S. Appl. No. 14/539,442, filed Nov. 12, 2014.
Aspect Imaging Ltd., "Cage in an MRD With a Fastening/Attenuating System", co-pending U.S. Appl. No. 14/527,950, filed Oct. 30, 2014.
Aspect Imaging Ltd., "System and Method for Generating Invasively Hyperpolarized Images", co-pending U.S. Appl. No. 14/556,654, filed Dec. 1, 2014.
Aspect Imaging Ltd., "System and Method for Generating Invasively Hyperpolarized Images", co-pending U.S. Appl. No. 14/554,682, filed Dec. 1, 2014.
Rapoport, Uri, "RF Shielding Conduit in an MRI Closure Assembly", co-pending U.S. Appl. No. 14/574,785, filed Dec. 18, 2014.
Aspect Imaging Ltd., "Foamed Patient Transport Incubator", co-pending U.S. Appl. No. 14/531,289, filed Nov. 3, 2014.
Aspect Imaging Ltd., "Mechanical Clutch for MRI", co-pending U.S. Appl. No. 14/611,379, filed Feb. 2, 2015.
Aspect Imaging Ltd., "Incubator Deployable Multi-Functional Panel", co-pending U.S. Appl. No. 14/619,557, filed Feb. 11, 2015.
Aspect Imaging Ltd., "MRI Thermo-Isolating Jacket", co-pending U.S. Appl. No. 14/623,039, filed Feb. 16, 2015.
Aspect Imaging Ltd., "MRI RF Shielding Jacket", co-pending U.S. Appl. No. 14/623,051, filed Feb. 16, 2015.
Aspect Imaging Ltd., "Capsule for a Pneumatic Sample Feedway", co-pending U.S. Appl. No. 14/626,391, filed Feb. 19, 2015.
Aspect Imaging Ltd., "Incubator's Canopy With Sensor Dependent Variably Transparent Walls and Methods for Dimming Lights Thereof", co-pending U.S. Appl. No. 14/453,909, filed Aug. 7, 2014.
Aspect Imaging Ltd., "Temperature-Controlled Exchangeable NMR Probe Cassette and Methods Thereof", co-pending U.S. Appl. No. 14/504,890, filed Oct. 2, 2014.
Aspect Imaging Ltd., "NMR Extractable Probe Cassette Means and Methods Thereof", co-pending U.S. Appl. No. 14/504,907, filed Oct. 2, 2014.
Aspect Imaging Ltd., "Means for Operating an MRI Device Within a RF-Magnetic Environment", co-pending U.S. Appl. No. 14/596,320, filed Jan. 14, 2015.
Aspect Imaging Ltd., "Means and Method for Operating an MRI Device Within a RF-Magnetic Environment", co-pending U.S. Appl. No. 14/596,329, filed Jan. 14, 2015.
Aspect Imaging Ltd., "CT/MRI Integrated System for the Diagnosis of Acute Strokes and Methods Thereof", co-pending U.S. Appl. No. 14/598,517, filed Jan. 16, 2015.
Aspect Imaging Ltd., "RF Automated Tuning System Used in a Magnetic Resonance Device and Methods Thereof", co-pending U.S. Appl. No. 14/588,741, filed Jan. 2, 2015.
Aspect Imaging Ltd., "Method for Manipulating the MRI's Protocol of Pulse-Sequences", co-pending U.S. Appl. No. 14/070,695, filed Nov. 4, 2013.

MRI WITH MAGNET ASSEMBLY ADAPTED FOR CONVENIENT SCANNING OF LABORATORY ANIMALS

CROSS REFERENCE TO RELATED APPLICATIONS

This application is a Continuation of U.S. application Ser. No. 14/581,266, filed on Dec. 23, 2014, which is a Continuation-in-Part of U.S. application Ser. No. 13/241,378, filed on Sep. 23, 2011, which claims the benefit of U.S. Provisional Application No. 61/387,538, filed on Sep. 29, 2010, all of which are incorporated herein by reference in their entirety.

FIELD OF THE INVENTION

The present invention generally pertains to MRI with magnet assembly adapted for convenient scanning of laboratory animals, containing an automated RF tuning unit.

BACKGROUND OF THE INVENTION

Commercially available MRI devices typically consist of main magnets which are positioned in parallel and horizontally. Surface coils (also known as surface plates) are essentially loops of conducting material, such as copper tubing. Surface coils are commonly positioned in a plane being substantially perpendicular to the plane of the main magnets. The surface coils are placed directly on or over the region of interest for increased magnetic sensitivity, more information is available at http://www.mr-tip.com.

The positioning of the coil is an important determinant of performance. As only the region close to the surface coil will contribute to the signal, there is an improvement in the signal to noise ratio for these regions, compared to the use of receiver coils that surround the appropriate part of the body. These coils are specifically designed for localized body regions, and provide improved signal to noise ratios by limiting the spatial extent of the excitation or reception.

The effective free space within an MRI device, especially lab-scale and experimental MRI devices is very much limited. The distance between the scanned object and the main magnet is significantly wider as compared with the distance to the surface coils. This is truer when surface coils are utilized. Scanned objects, as such as neonates and laboratory animals, e.g., rats and mice, are preferably scanned when they are immobilized in a perfect horizontal configuration. When main magnets are positioned horizontally, surface coils are usually positioned vertically. The irregular body of the animal to be scanned is somewhat compressible along the vertical plane whilst it is substantially non compressible along the horizontal plane. Hence, either the MRI device is designed to be big enough to accommodate the object, and thus the device is much more expensive, or the scanning resolution is relatively low.

A few patents disclose means for overcoming those drawbacks, and present methods for positioning and securing the RF surface coil at a predetermined configuration. Hence for example, U.S. Pat. No. 5,085,219 ('219) discloses an adjustable holder for a magnetic resonance imaging RF surface coil for imaging a part of the body such as the temporomandibular joint. Elements are provided for positioning and securing the RF surface coil at a first predetermined point along a longitudinal axis of the holder and for positioning and securing the RF surface coil at a second predetermined point transverse to the longitudinal axis and at a radial distance R from the longitudinal axis. Patent '219 shows that the surface coil may be adjusted along a path transverse to the longitudinal axis by way of an adjustable shaft or arm which can be moved inwardly and outwardly, and the surface coil can be pivoted in a step-wise manner using a pivot head having a plurality of equally spaced detents. This technology is not implementable in small laboratory-scale MRI devices and scanned object must be tilted and otherwise maneuvered such that optimal imaging is obtained.

The magnetic field produced by the MRI device is sensitive to manufacturing process variability of the magnets as well as to the ambient temperature of the examination area. Therefore, the frequency of the magnetic field, generated by an MRD's main magnets, changes from one venue to another and from one operation to another, and even once in every few scanning operations. Radiofrequency transmitted by the RF coil assembly needs to match the main magnetic field in order to receive a good signal, low noise and sharper images. The variability in the magnetic field is compensated by tuning the frequency of the electromagnetic radiation transmitted by the RF coils. Currently, this tuning mechanism involves manually mechanically adjusting the location of the RF coils with respect to the magnetic field, thereby causing a change in the RE field. Such manual systems involve trial and error and are prone to elaborate and lengthy calibration.

None of the above provides a simple solution for precise positioning of the animal within an MRI device. Hence an MRI-compatible and positioning system fulfill a long felt need. In addition, an automated RF coil tuning unit, provided to replace manual calibration of the RF field, also fulfills a long felt need.

SUMMARY OF THE INVENTION

It is thus one object of the invention to disclose an MRD comprising a plurality of main magnets positioned in a substantial horizontal plane and a plurality of surface plates or coils magnets positioned in a substantial vertical plane. Another object is to disclose a method of using the same such that improved MRI scans are obtained.

BRIEF DESCRIPTION OF THE DRAWINGS

Preferred embodiments of the current invention are described herein below with reference to the following drawings.

DETAILED DESCRIPTION OF THE PREFERRED EMBODIMENTS

The following description is provided in order to enable any person skilled in the art to make use of the invention and sets forth the best modes contemplated by the inventor of carrying out this invention. Various modifications, however, will remain apparent to those skilled in the art, since the generic principles of the present invention have been defined specifically to provide an MRI device with a plurality of enter ports and to methods using the same.

The term 'Magnetic Resonance Device' (MRD) specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) spectroscope or any combination thereof. The MRD hereby disclosed is optionally a portable MRI device, such as the ASPECT Magnet Technologies Ltd commercially available devices, or a commercially available non-portable device. The MRD hereby disclosed is optionally a lab-scale or experimental MRI device.

As used herein, the term "animal" or "mouse" generally refers in an interchangeable manner to any living creature, such as neonates, other mammal such as mice, rats, cats, dogs, rabbits etc and laboratory animals.

As used herein, the term "plurality" refers in a non-limiting manner to any integer equal or greater than 1.

As used herein, the term "motor" generally refers to any kind of an electric motor, namely a machine converting electrical energy into mechanical energy.

As used herein, the term "console" generally refers to a system console, computer console or root console which is the physical device consisting of a keyboard and a screen and computer containing an operating system program.

As used herein, the term "memory means" generally refers to any physical device used to store programs (sequences of instructions) or data (e.g. program state information) on a temporary or permanent basis for use in a computer or other digital electronic device.

The automated tuning unit disclosed by the present invention recites some main principles; the tuning can be made by semiautomatic manner (i.e. manually operating the motor by controlling commands given by a user) or in an automatic manner by a fully automatic cycle called by one command of the user. The solution combines memory means assembled on the coil which identify the connected coil and stores information about several calibration parameters which are used during the auto-tuning (AT), together with firmware that supports communication with a console. The tuning takes place by mechanically adjusting the location or position of the RF coil assembly with respect to the main magnetic field. AT supporting coils are equipped with a coil status indication led and bed illumination led for operating convenience.

Figure 1:
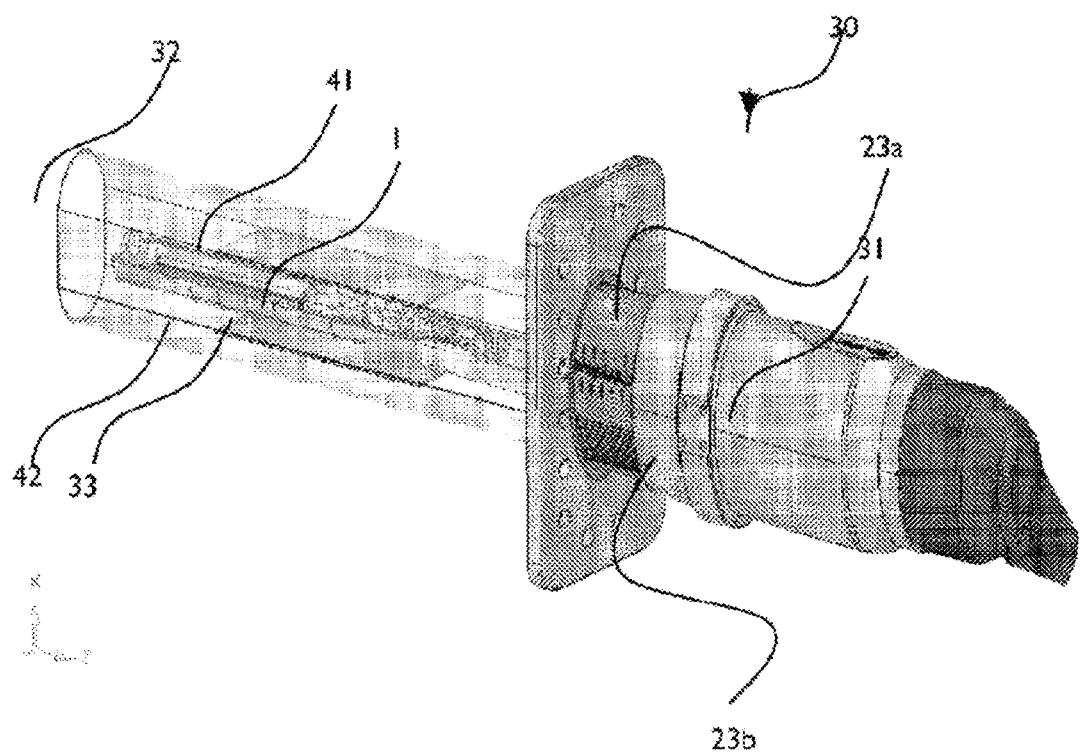
FIG. 1 shows a detailed view of a Mouse Housing System (MHS), in accordance with a preferred embodiment of the present invention.

Reference is now made to FIG. 1, schematically illustrating (not to scale) a detailed view of MHS 30. MHS is characterized by a proximal maneuverable portion 31, close to the operator, and a distal portion, insertably provided within the MRD. This inner portion, made of MRI-compatible materials, such as polymers, comprises inter alia a cradle or bed-like member 33, on which a scanned animal 1 is horizontally immobilized. In this drawing, the animal and its cradle are encapsulated within a plastic cover 32. A plurality of surface coils is intimately covering the animal. Main magnets of MRD are positioned vertically (not shown), and thus surface coils or surface plates 41, 42 are positioned horizontally, gently clutching animal 1 in a vertical plane, namely from top and bottom.

It is acknowledged in this respect that laboratory animals, such as rodents and similar, have a skeleton that allow them to be pressed to some extent along their sagittal plane, whilst animals such as humans and other primates cannot be substantially pressed naturally along their coronal nor transverse planes.

Reference is again made to FIG. 1, schematically illustrating (not to scale) MHS 30 in a distal (40 mm) & horizontal (180°) configuration, i.e., animal 1 is reciprocally displaced distally, towards a wall where cradle 33 immobilizing the animal is place horizontally. Indicia 23a and 23b indicate the same.

Figure 2A:
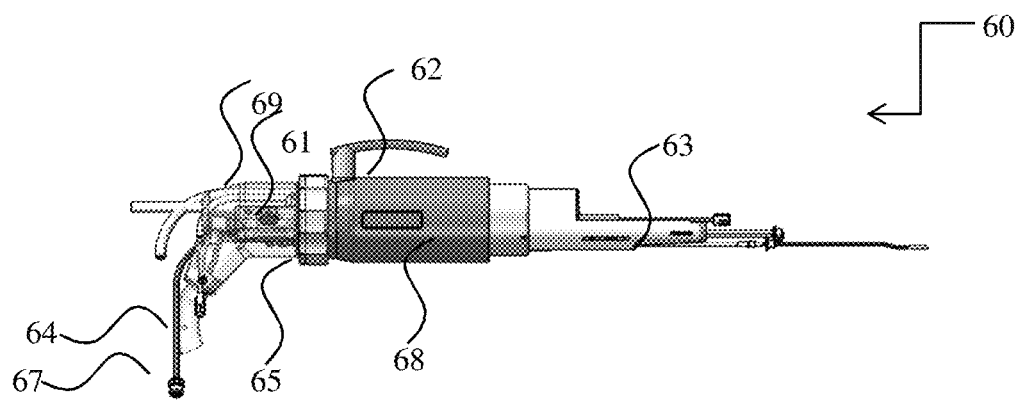
FIG. 2A and FIG. 2B illustrates in an out-of-scale manner an embodiment of the high level assembly comprising the automated tuning unit and the MHS.
Figure 2B:
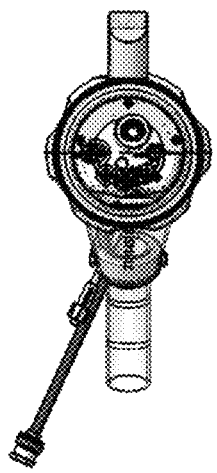

Reference is now made to FIG. 2A and FIG. 2B, schematically illustrating in an out of scale manner the high level assembly 60 comprising the automated tuning unit 61 and the MHS 63. FIG. 2A and FIG. 2B illustrate the front and side view of the assembly, respectively. The tuning unit is preferably positioned on the proximal portion of the MHS as disclosed by the present invention. The tuning unit 61 is automatically operable by a motor, preferably a DC step motor.

The automated tuning unit and its surrounding components, collectively referred to as the automated tuning assembly, are preferably put together in an end cover 69. The automated tuning assembly is connected through the proximal end of the end cover to the MHS via a tube press assembly 68. The tube press assembly is configured to connect to the tuning assembly on its distal end and connect to the MHS on its proximal end. The connection may take place via a connector 65, which may be in a non-limiting example a nut connector, twist-on connector and/or an end ring. The tube press assembly may further comprise a locking component 62, provided for locking of the MHS in place with the tube press assembly and the automated tuning assembly. In some embodiments, the tuning unit may further comprise a cable organizer 64, which is connected to the distal end of the end cover 69.

In an embodiment, the tuning unit may also be operable by manual manipulation which includes tuning the RF frequency by mechanically modulating an RF modulating component 67, without using the motor.

In a preferred embodiment, information and data may be stored on a memory means, pertaining to calibration related parameters, including the RF coil serial number, the RF coil type in a decimal value, the RF coil name in ASCII text, a decimal value parameter for coil motor calibration, tuning range frequency limits and any other RF related parameters.

In an embodiment, the automated tuning system may include a status indicator, which for example could be a visual indicator such as one or more LEDs, to provide feedback to an operator as to the status of the current working state of the automated tuning unit and the state of the RF coil.

Figure 3:
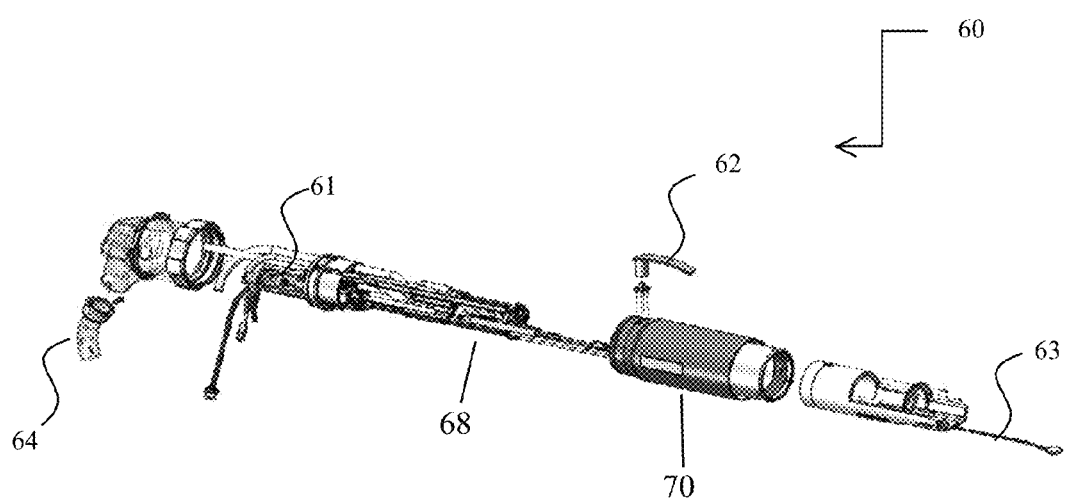
FIG. 3 illustrates an explosive view of the tuning assembly as shown in FIG. 2.

Reference is now made to FIG. 3 illustrating in an out of scale manner an explosive view of the tuning assembly as shown in FIG. 2; FIG. 3 shows the integrated system subassembly comprising the RF coil assembly 70 and adapted to be in mechanical connection with MHS 63 via the tube press assembly 68.

Figure 4:
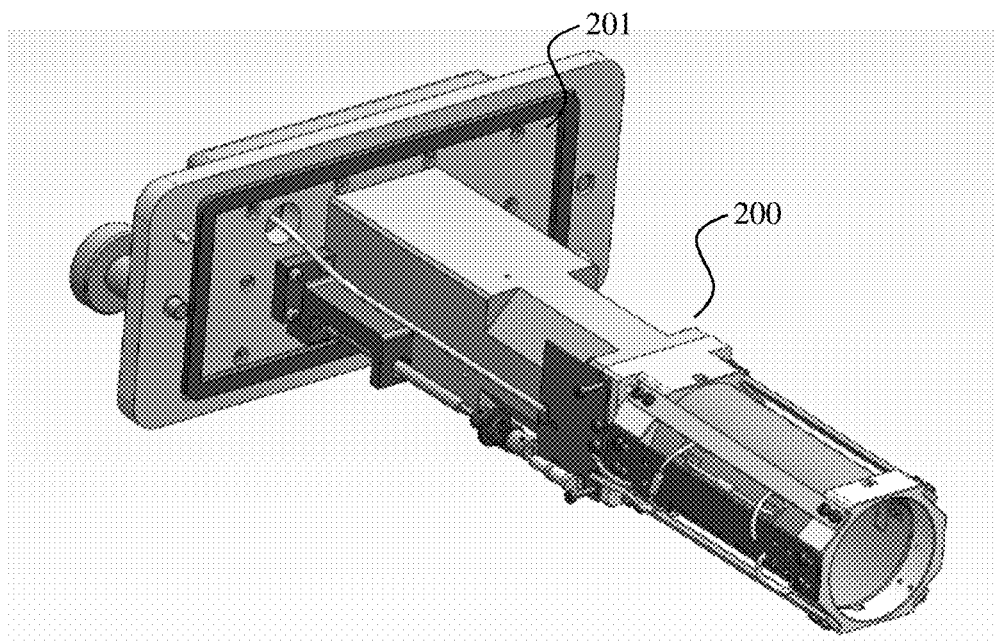
FIG. 4 illustrates a view of the motor drive shaft.

Reference is now made to FIG. 4 illustrating the motor drive shaft 200. The shaft is designed to contain and accommodate the automated tuning assembly as disclosed in FIG. 2. The proximal end of the motor drive shaft is adapted for connecting to the tube press assembly 68. The distal end of the motor drive shaft is designed for connecting to the MRD port cover 201.

Figure 5:
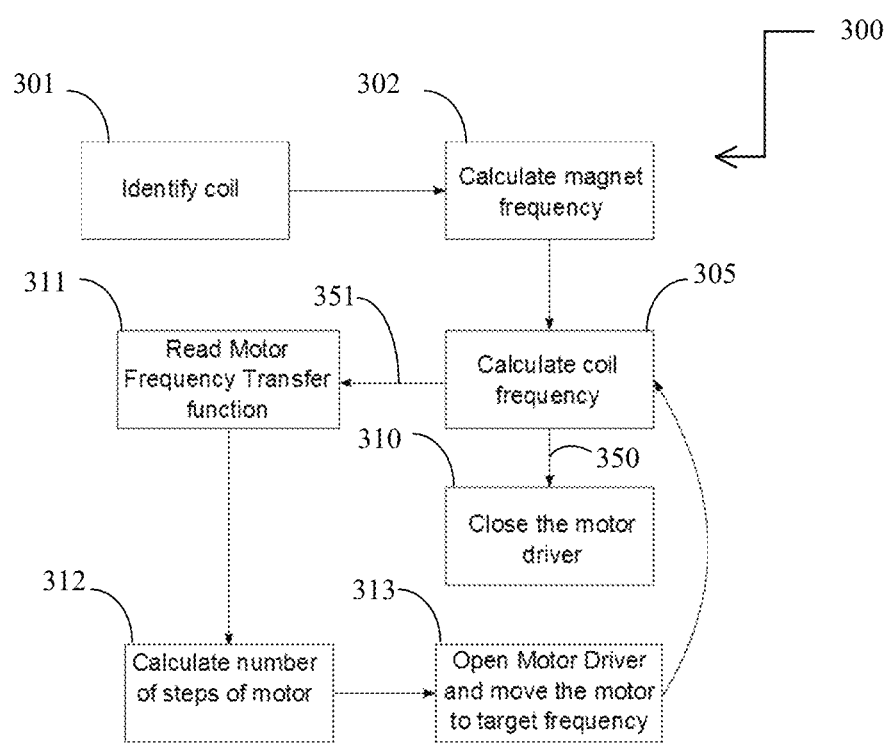
FIG. 5 illustrates the automatic tuning algorithm.

Reference is now made to FIG. 5 disclosing the automatic tuning algorithm 300 of the automated tuning system disclosed by the present invention. The algorithm starts by identifying the RF coil 301 through the memory means comprised in the RF coil and containing coil calibration parameters. Next, the main magnetic field frequency is measured and compared to the measured RF coil transmitted frequency 302. If the frequencies match 350, the algorithm shuts down the motor drive 310. However, if the frequencies do not match 351, then the algorithm proceeds to reading the Motor Frequency Transfer function 311, which assigns a conversion function for each identified RF coil for translating the desired frequency modulation into executable motor steps. The function is then used for calculating the number of steps the motor needs to execute 312, which is followed by opening the motor driver and moving the motor to target the frequency 313 to match the magnetic frequency. The algorithm then returns to step 305 of calculating the RF coil frequency and comparing it to the main magnetic field frequency.

Figure 6:
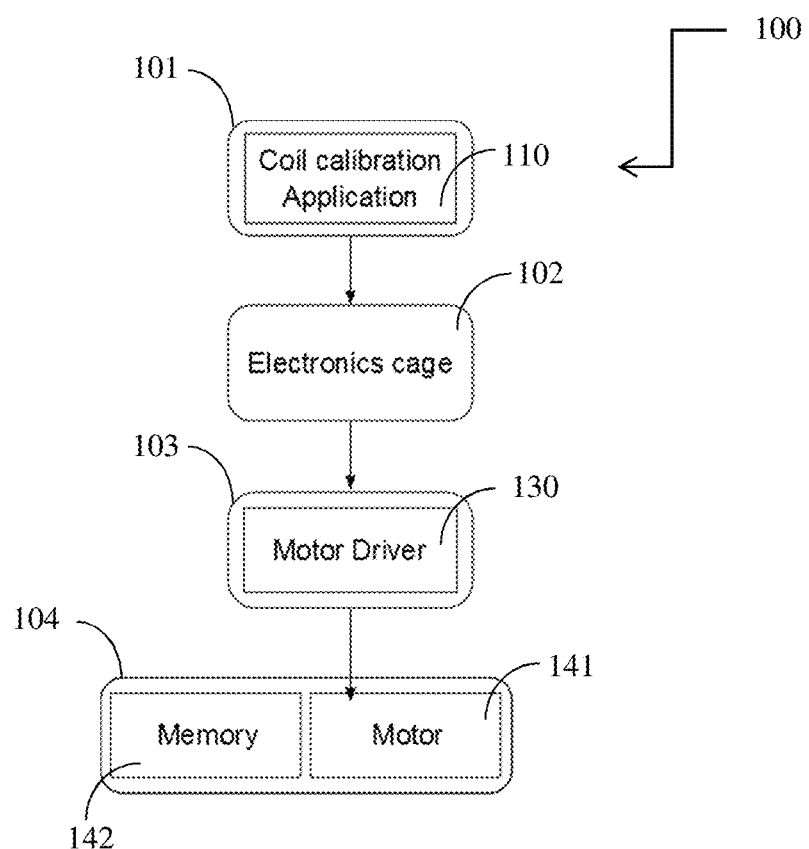
FIG. 6 illustrates the automatic tuning system.

Reference is now made to FIG. 6, showing an automatic tuning system 100. The present invention is employed in an MRD system. The MRD system includes a console 101 having a display, a keyboard and includes a processor that is a commercially available programmable machine running a commercially available operating system. The processor contains the coil calibration application 110 which comprises instructions for tuning the RF frequency via the motor. The console 101 and an electronic cage 102 of the MRD system are connected to communicate with each other. The console 101 provides the user an interface that enables automatic and/or semiautomatic commands to be transmitted into the electronic cage 102. The motor driver 130 found in the MRD magnet 103 functions in response to instructions transmitted from the console 101 through the electronics cage 102 to operate the motor 141 residing in the coil 104. The coil further comprises a memory means 142 for storing coil calibration information and data.

In various embodiments, the console 101 of the MRD may be operable by using a mouse, a keypad, touch screen, voice activated and such. The tuning unit may also be remotely controlled.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The invention claimed is:

1. A method for positioning an immobilized animal in a predefined configuration, comprising:
    providing an animal handling system (AMS), comprising:
        a proximal portion having at least one inner shaft and at least one outer shaft, said at least one outer shaft is telescopically maneuverable with said at least one inner shaft to provide a telescopic mechanism;
    providing said AMS with a distal portion comprising a configurable encapsulated life support system (ELSS), said ELSS is rotatable about a longitudinal axis of said at least one inner shaft and at least one outer shaft and translationally maneuverable parallel to said longitudinal axis by means of said maneuverable said telescopic mechanism; and
    providing said proximal portion of said AMS having indicia indicating a linear displacement and a rotational displacement of said ELSS, such that said ELSS is accurately and reversibly configured within said medical device to optimize animal analyses,
    wherein said method further comprises the steps of:
    a. providing an automated tuning unit comprising a motor,
    b. calculating a first frequency of said magnetic field,
    c. calculating a second frequency of said RF coil source, and
    d. dislocating said at least one RF coil by said motor, thereby matching said first frequency to said second frequency.

2. The method according to claim 1, wherein said medical device is an MRD.

3. The method according to claim 1, wherein said AGN and said FSM are adapted by means of size and shape, to ensure anaesthetization of laboratory animals.

4. The method according to claim 1, wherein said step of controlling said motor is provided automatically, semiautomatically or manually.

5. The method according to claim 1, further comprising storing in a computer readable medium identification data of said RF coil and information on calibration related parameters.

6. The method according to claim 1, further comprising indicating the status of said calibrations by a status indicator.

* * * * *